United States Patent
Zhong et al.

(10) Patent No.: US 10,238,408 B2
(45) Date of Patent: Mar. 26, 2019

(54) ACOUSTIC LENS FOR SHOCK WAVE LITHOTRIPSY AND RELATED METHODS

(75) Inventors: Pei Zhong, Chapel Hill, NC (US); Glenn M. Preminger, Chapel Hill, NC (US); Georgy N. Sankin, Durham, NC (US); Franklin Hadley Cocks, Durham, NC (US); Walter Neal Simmons, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 865 days.

(21) Appl. No.: 13/400,446

(22) Filed: Feb. 20, 2012

(65) Prior Publication Data

US 2012/0215138 A1    Aug. 23, 2012

Related U.S. Application Data

(63) Continuation of application No. PCT/US2010/026654, filed on Mar. 9, 2010.

(60) Provisional application No. 61/274,632, filed on Aug. 19, 2009.

(51) Int. Cl.
*A61H 1/00* (2006.01)
*A61B 17/225* (2006.01)
*A61B 17/22* (2006.01)

(52) U.S. Cl.
CPC ...... *A61B 17/225* (2013.01); *A61B 17/22004* (2013.01)

(58) Field of Classification Search
CPC .............................. A61B 17/2251; G10K 15/06
See application file for complete search history.

(56) References Cited

U.S. PATENT DOCUMENTS

| 6,491,685 B2 | 12/2002 | Visuri et al. |
| 2001/0023326 A1 | 9/2001 | Spector |
| 2005/0038361 A1 | 2/2005 | Zhong et al. |

FOREIGN PATENT DOCUMENTS

| EP | 1354561 A1 | 10/2003 |
| EP | 1 445 003 | 8/2004 |

(Continued)

OTHER PUBLICATIONS

International Search Report for PCT Application No. PCT/US2010/026654 dated May 5, 2010.

(Continued)

*Primary Examiner* — Hien Nguyen
(74) *Attorney, Agent, or Firm* — Jenkins, Wilson, Taylor & Hunt, P.A.

(57) ABSTRACT

Systems and methods for providing therapeutic shock waves are provided. A modified acoustic lens can include a first lens portion for directing a first part of an acoustic shock wave pulse toward a target and a second lens portion for directing a second part of the acoustic shock wave pulse toward the target. The second lens portion can be offset relative to the first portion such that transmission of the second part of the acoustic shock wave pulse through the second lens portion is delayed by a predetermined amount relative to transmission of the first part through the first lens portion. In situ superposition of the first and second pulses near and at the target can lead to the formation of a pressure waveform with idealized pulse profile and broadened focal width, which can provide for improved comminution of a concretion located within a living body with reduced tissue injury.

9 Claims, 6 Drawing Sheets

(56) References Cited

FOREIGN PATENT DOCUMENTS

EP 2467071 6/2012
WO WO 2011/022085 2/2011

OTHER PUBLICATIONS

Extended European Search Report for Application No. 10810298.9 dated Nov. 29, 2013.
Communication of European publication number and information on the application of Article 67(3) EPC for Application Serial No. PCT/US20100026654 dated May 31, 2012.
IPRP and Written Opinion with ISR for Application No. PCT/U82010/026654 dated Feb. 21, 2012.

ACOUSTIC LENS FOR SHOCK WAVE LITHOTRIPSY AND RELATED METHODS

CROSS-REFERENCE TO RELATED APPLICATIONS

This application is a continuation of and claims priority to PCT/US2010/026654 filed Mar. 9, 2010, which claims the benefit of and priority to U.S. Provisional Application No. 61/274,632, filed Aug. 19, 2009, the entire disclosures of which are incorporated herein by reference in their entireties.

GOVERNMENT INTEREST

This invention was made with government support under Grant No. 5R01DK052985 awarded by United States National Institutes of Health. The government has certain rights in the invention.

TECHNICAL FIELD

The subject matter disclosed herein relates generally to systems and methods for providing therapeutic shock waves. More particularly, the subject matter disclosed herein relates to designs for acoustic lenses for use in shock wave lithotripsy.

BACKGROUND

Shock wave lithotripsy is a non-invasive method for the treatment of renal calculi (kidney stones), biliary calculi (stones in the gallbladder or in the liver), and the like. In early systems for extracorporeal stone fragmentation, generally referred to as electrohydraulic shock wave lithotripsy, a probe (or electrode) containing two conical tips separated by a small distance (e.g., about 1 mm) is used for shock wave generation. When electric current is passed between the tips of the electrode, a spark is created that vaporizes the water or other surrounding fluids to create a shock wave. For example, U.S. Pat. No. 3,942,531 to Hoff et al. discloses the use of a spark gap discharge in water to generate a shock wave within an ellipsoidal reflector that collects and focuses the shock wave to fragment kidney stones inside the body. Such systems are generally effective in treatment, but the electrodes are prone to deterioration and thus need to be replaced periodically. The replacement of the electrodes is an added cost, an additional task to be performed during the course of a treatment, and an increase in the total amount of time necessary to complete the lithotripsy process.

By comparison, electromagnetic shock wave lithotripters use the rapid vibration of thin metallic membranes driven by electromagnetic forces to generate a shock wave rather than electric spark discharges. For instance, U.S. Pat. No. 4,655,220 to Hahn et al. discloses a device using a coil and a mating radiator, in the form of a spherical segment, to produce magnetically induced self-converging shock waves. Because the electromagnetic shock source does not deteriorate like the electrodes of the electrohydraulic shock wave lithotripters, use of electromagnetic shock wave lithotripters can provide time savings by not requiring the frequent replacement of the shock wave generating element. It has been shown, however, that electromagnetic shock wave lithotripters are often not as effective in stone comminution and patient outcome compared to first-generation electrohydraulic shock wave lithotripters, such as the original Dornier HM-3 lithotripters.

This deficiency is at least in part caused by the significant difference between the profile of pressure waveforms and lithotripter focal width (defined as extent of −6 dB contour of maximum peak positive pressure in the lithotripter focal plane) of electromagnetic and electrohydraulic systems. Specifically, whereas the pressure waveform produced by an electrohydraulic lithotripter consists of a leading compressive wave followed by a tensile wave, the pressure waveform produced by an electromagnetic lithotripter typically has an additional secondary compressive followed by an additional tensile wave of low amplitude at the end. The secondary compressive and tensile waves are caused by current oscillation produced during the energy discharge, an inherent feature of all electromagnetic shock wave lithotripters.

Methods and systems have been developed to modify and augment the operation of traditional shock wave lithotripters to at least partially account for the drawbacks inherent in both electrohydraulic and electromagnetic systems, but such systems can require additional components that add time and cost in setting up the lithotripter system. For instance, U.S. Pat. No. 5,224,468 to Grünewald et al. discloses an arrangement for generating focused shock waves from a combination shock wave source that can include a mixture of electrohydraulic, electromagnetic, and piezoelectric sources. Although the multiple shock wave sources can be set to define a time delay between pulses, such a complex system can require precise control and calibration of the multiple sources, and if an electrohydraulic source is included, all of the drawbacks to this technology remain. U.S. Pat. No. 4,972,826 to Koehler et al. describes an electromagnetic shock wave lithotripter in which one or more plates are inserted between the shock wave generator and the acoustic lens to modify the chronologically-varying pressure curve experienced at the focus of the shock wave lithotripter. These systems require additional components that must be properly aligned and adjusted within the system. Further, U.S. Pat. No. 4,664,111 to Reichenberger discloses a shock wave tube for generating time-staggered shock waves by means of a splitting device, such as a cone, for the fragmentation of concrements in vivo. Reichenberger discloses that the effects of the shock waves can be improved if they are so closely spaced in time that they overlap in their action on the concrement. The effects of shock wave induced cavitation are not disclosed by Reichenberger.

In addition, U.S. Pat. Nos. 5,582,578, 5,800,365, and 6,770,039 to Zhong et al., the disclosures of which are incorporated herein by reference in their entireties, each disclose methods for the comminution of concretions in vivo by controlling and concentrating cavitation energy utilizing two shock wave pulses separated by a short time delay. These methods are directed to using the second pulse to force the collapse of cavitation bubble clusters produced by the first pulse in such a way that the cavitation collapse energy is directed towards the target concretion and thereby reduce tissue injury caused by random collapse of cavitation bubbles. The multiple pulses of these methods, however, are created by modifications to a single shock-wave spark source or by the use of multiple shock-wave spark sources to create separate shock wave pulses. Furthermore, these methods generate the shock-waves using electrohydraulic systems rather than electromagnetic systems. The generation of multiple shock-wave pulses in electromagnetic systems would require a novel and entirely different physical principle to that used previously.

SUMMARY

In accordance with this disclosure, systems and methods for providing therapeutic shock waves are described. Such systems and methods can advantageously be used to provide shock waves via a new and novel principle for modifying the characteristics of the lithotripter field, optimizing the profile of the pressure waveform, and/or broadening the focal width of the lithotripter pulse to provide effective stone comminution with minimal tissue injury to the patient.

For instance, in one aspect, an acoustic lens for an electromagnetic shock wave lithotripter is provided. The acoustic lens can include a first lens portion for directing a first part of an acoustic shock wave pulse toward a target and a second lens portion for directing a second part of the acoustic shock wave pulse toward the target. The second lens portion can be offset relative to the first lens portion such that transmission (or reflection) of the second part of the acoustic shock wave pulse through (or by) the second lens portion is delayed by a predetermined amount relative to transmission (or reflection) of the first part of an acoustic shock wave pulse through (or by) the first lens portion, based on geometrical acoustics principle. Alternatively, these lenses can be produced using reflective and transmissive acoustic elements, just as telescopes can be produced with either reflective optics or with transmissive and reflective optics.

In another aspect, a system for shock wave lithotripsy is provided. The system can include an electromagnetic shock wave pulse generator for generating an acoustic shock wave pulse and an acoustic lens positioned between the electromagnetic shock wave pulse generator and a target. The acoustic lens can include a first lens portion for directing a first part of an acoustic shock wave pulse toward the target and a second lens portion for directing a second part of the acoustic shock wave pulse toward the target. The second lens portion can be offset relative to the first lens portion such that transmission of the second part of the acoustic shock wave pulse through the second lens portion is delayed by a predetermined amount relative to transmission of the first part of an acoustic shock wave pulse through the first lens portion.

In another aspect, a method for shock wave lithotripsy is provided. The method can include generating a shock wave, separating the shock wave into a multi-pulsed shock wave including a first acoustic shock wave pulse and a second acoustic shock wave pulse, focusing the first acoustic shock wave pulse to a focus, and focusing the second acoustic shock wave pulse to the focus. Each of the first and second acoustic shock wave pulses can have a leading compressive component, a tensile component, and a trailing compressive component, but with the second acoustic shock wave pulse being delayed from the first acoustic shock wave pulse by a predetermined time interval. In this way, the trailing compressive component of the first acoustic shock wave pulse can be reduced or eliminated by in situ pulse superposition with the tensile component of the trailing second acoustic shock wave pulse.

In another aspect, another method for shock wave lithotripsy is provided. The method can include generating a shock wave, and separating the shock wave into a multi-pulsed shock wave including a first acoustic shock wave pulse and a second acoustic shock wave pulse, where the second acoustic shock wave pulse is delayed from the first acoustic shock wave pulse by a predetermined time interval. The method can further include focusing the first acoustic shock wave pulse toward a target, focusing the second acoustic shock wave pulse toward the target, and superimposing the first shock wave pulse and the second shock wave pulse to produce a modified waveform leading to a modified shock wave pulse with a broader focal width than each of the individual unmodified shock wave pulses.

In another aspect, yet another method for shock wave lithotripsy is provided. The method can include generating an acoustic shock wave from an electromagnetic shock wave source, the acoustic shock wave comprising a first compressive wave, a first tensile wave, a second compressive wave, and a second tensile wave. The method can further include modifying the acoustic shock wave to minimize the second compressive wave and the second tensile wave while broadening the focal width of the acoustic shock wave.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

The present subject matter provides systems and methods for providing therapeutic shock waves for shock wave lithotripsy. In one aspect, the present subject matter provides a new geometry for an acoustic lens that can generate a more desirable waveform with broader focal width for a given acoustic pulse energy. This geometry can permit the formation of two shock waves that are separated in their propagation and arrival time at the lithotripter focus by a few microseconds. By proper acoustic lens design, the time-delayed superposition of these two shock waves can allow in situ pulse superposition to alter the profile of the pressure waveform while also enlarging simultaneously the focal width of the lithotripter.

Figure 1:
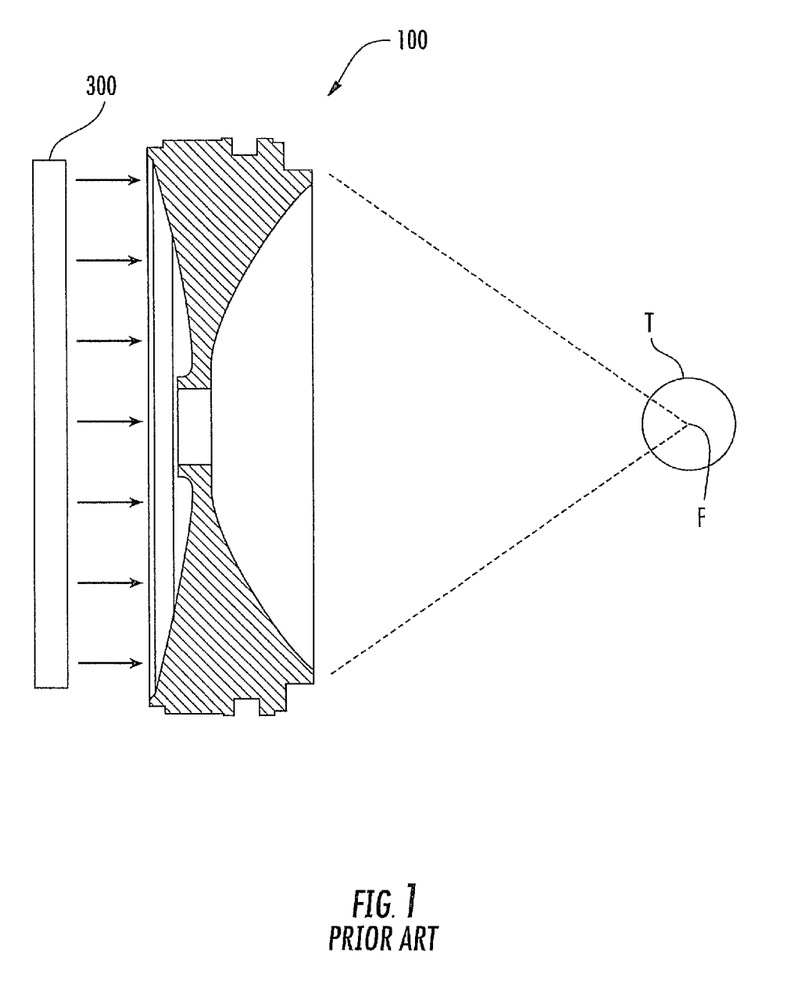
FIG. 1 is a side view of a prior art acoustic lens for use in shock wave lithotripsy.

FIG. 1 shows a design for a typical acoustic lens, generally designated 100, for use in an electromagnetic shock-wave lithotripter. Previous acoustic lens 100 can have a generally concave lens shape for focusing the acoustic pulse towards the target of the lithotripter. As discussed above, this previous lens design does not provide any compensation for the oscillating pattern of multiple compressive and tensile waves produced by the shock-wave source. The acoustic lens design according the presently-disclosed subject matter does provide a mechanism to optimize the profile of the pressure waveforms produced by an electromagnetic shock-wave source and produce maximum pressures that can range from about 5 MPa to about 200 MPa.

Figure 2A:
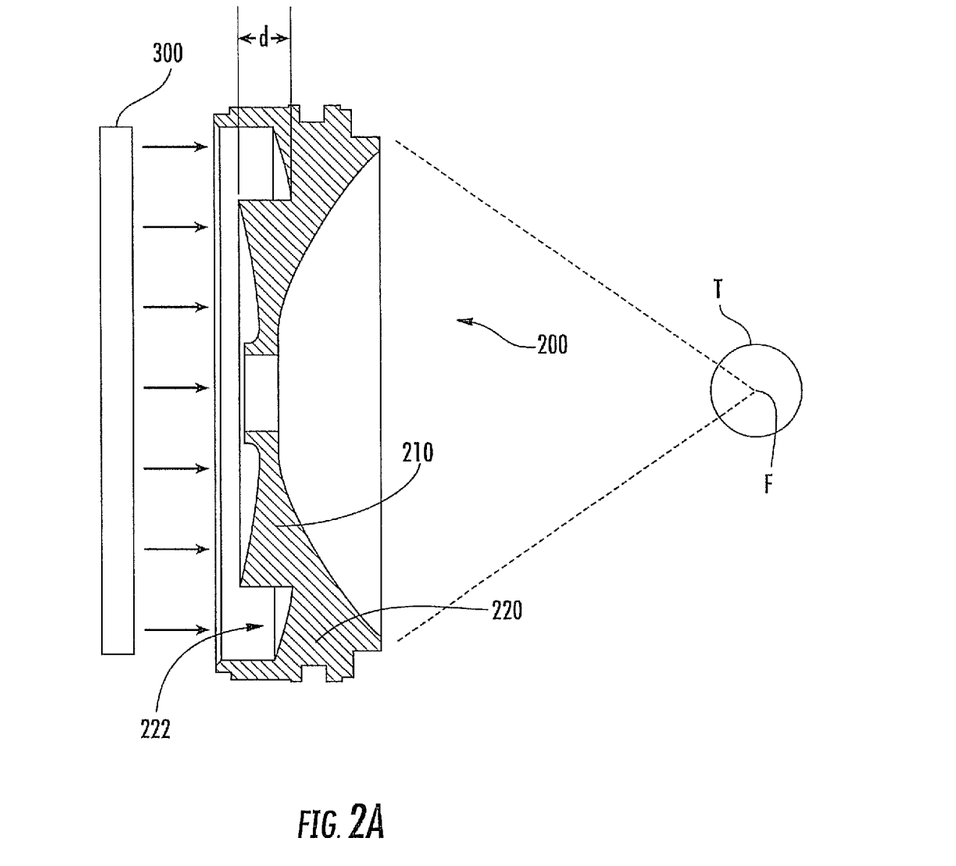
FIG. 2A is a side view of an acoustic lens according to an embodiment of the presently disclosed subject matter.
Figure 2B:
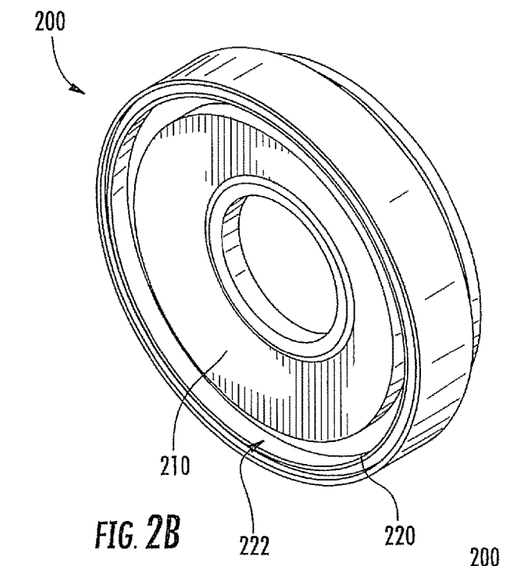
FIG. 2B is a perspective view of an acoustic lens according to the embodiment of FIG. 2A.
Figure 2C:
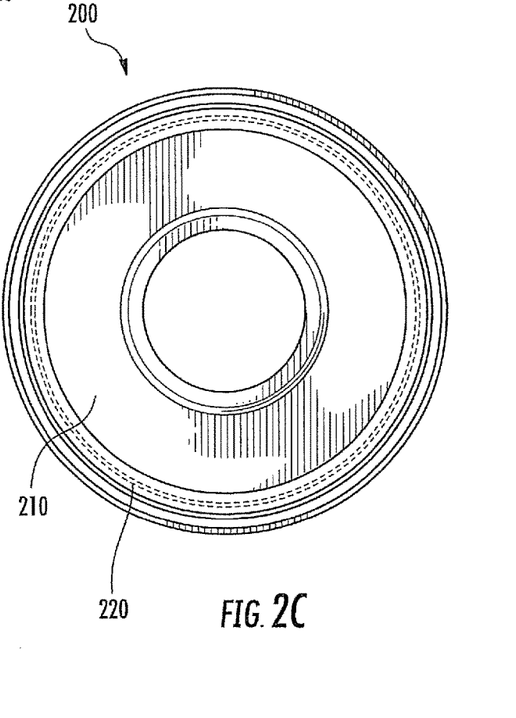
FIG. 2C is a top plan view of an acoustic lens according to the embodiment of FIG. 2A.

For instance, in one particular embodiment shown in FIGS. 2A-2C, an acoustic lens for use in shock wave lithotripsy, generally designated 200, can have a generally concave lens shape similar to acoustic lens currently in use for electromagnetic shock wave lithotripters, such as prior art acoustic lens 100, which can direct acoustic waves generated by a shock wave source 300 (e.g., an electromagnetic coil), towards a target T positioned at a beam focus F. A difference from current lens designs, however, is that a portion of the lens can be modified to alter acoustic transmission through that portion.

In particular, the surface of lens 200 can be partitioned into multiple sectors. For example, lens 200 can have a first lens portion 210 which can have a profile similar to a prior art acoustic lenses used for this purpose. Lens 200 can further have a second lens portion 220, which can have a generally narrower thickness than a corresponding portion of a typical acoustic lens. First lens portion 210 can comprise between about 40% and about 80% of a cross-sectional area of lens 200 (e.g., often between about 50% and about 70%), and second lens portion 220 can comprise the remaining area. First lens portion 210 and second lens portion 220 can have similar geometries but different thicknesses so that the incident planar acoustic waves are transmitted with different propagation times through each portion. This lens design can provide an idealized pressure waveform profile and energy distribution for improved comminution of a concretion located within a living body with reduced tissue injury.

Any of a variety of possible multi-portion lens configurations can be used to modify the pressure waveform in this way. For example, in one configuration shown in FIGS. 2A through 2C, first lens portion 210 can be a central portion of lens 200, and second lens portion 220 can be a truncated outer rim portion of lens 200. A groove 222 can be formed in an outer portion of second lens portion 220 of lens 200. More specifically, for example, groove 222 can be an annular space formed into the surface of second lens portion 220 facing shock wave source 300 and centered about the central axis of lens 200, as illustrated in FIGS. 2A through 2C. Alternatively in a similar configuration, groove 222 can have a different geometry, being formed in a portion of second lens portion 220 of lens 200 that faces target T (i.e., faces away from shock wave source 300).

Groove 222 can be formed in second lens portion 220 as part of the production of lens 200, or it can be cut into an already formed lens. Further, the specific geometry of groove 222 can also be varied to change the operation of lens 200. For instance, groove 222 can be formed to have a curved bottom surface for directing the transmission of acoustic waves toward target T. Specifically, for example, groove 222 can have a depth d that is substantially constant relative to the unaltered surface of second lens portion 220. Stated otherwise, a bottom surface of groove 222 can retain substantially the same shape (e.g., generally concave), the only difference being that the surface is shifted by depth d. For instance, in some configurations of groove 222, depth d can be between about 5 mm and 25 mm, with many configurations having a depth d of between about 10 mm and 20 mm. The specific size of depth d can be selected to achieve the desired acoustic pulse characteristics. For instance, the time delay between the first and second acoustic shock-wave pulses can be calculated based on the following relationship:

$$\Delta t = d\left(\frac{1}{c_0} - \frac{1}{c_{lens}}\right)$$

where $\Delta t$ is the time delay, $c_0$ is the speed of sound in the coupling fluid, and $c_{lens}$ is speed of sound in the lens material. As should be understood from this relationship, in designs where lens 200 is composed of a material through which acoustic waves can propagate faster than through the surrounding coupling fluid (i.e., where $c_{lens}$ is greater than $c_0$), the time delay is a positive value, indicating that acoustic waves take more time to propagate through second lens portion 220 than they would though an unaltered lens. As a result, depth d and the lens material can be selected such that a desired time delay is achieved. As discussed below, this time delay can be between about 1 μs to about 6 μs between the first and second acoustic shock-wave pulses.

In addition, it should be recognized that lens 200 can be composed of a material through which acoustic waves can propagate slower than through the surrounding coupling fluid, wherein $c_{lens}$ is less than $c_0$. In such an alternative configuration, the relative geometry of first lens portion 210 can be reconfigured, wherein first lens portion 210 is thinner than an unmodified lens, such that similar time delays can be achieved.

Figure 3A:
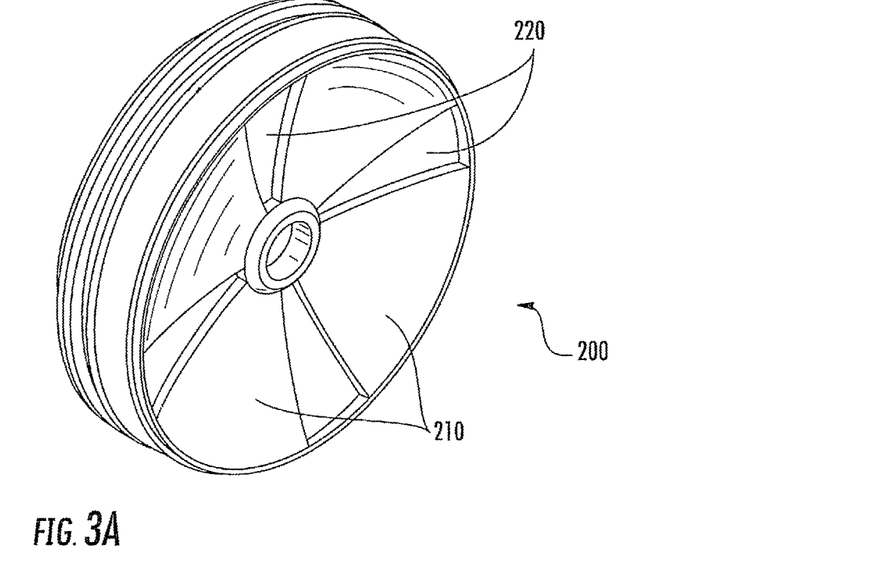
FIG. 3A is a perspective view of an acoustic lens according to another embodiment of the presently disclosed subject matter.
Figure 3B:
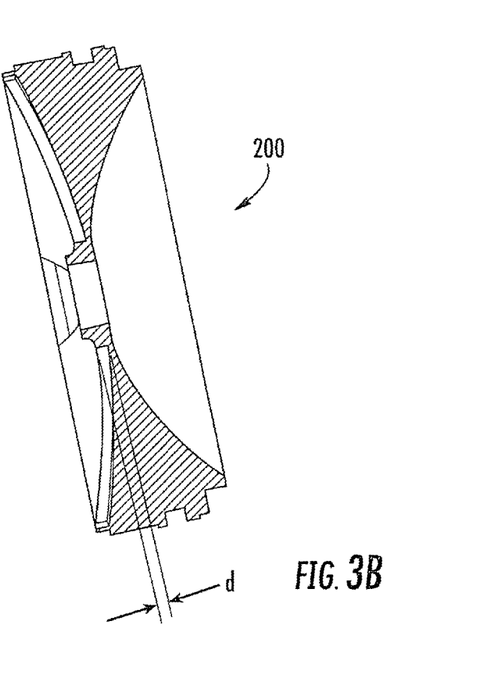
FIG. 3B is a side view of an acoustic lens according to the embodiment of FIG. 3A.

In another configuration shown in FIGS. 3A and 3B, first lens portion 210 and second lens portion 220 can comprise alternating circular sectors of lens 200. For example, as is illustrated in FIG. 3A, first lens portion 210 can include four sectors evenly distributed about the center of lens 200, each of the sectors of first lens portion 210 occupying an arc of lens 200 between about 30° to 75°. Second lens portion 220 can likewise include four sectors distributed about the center of lens 200 between the sectors of first lens portion 210. Similar to the configuration discussed previously, a surface of second lens portion 220 can be offset relative to the surface of first lens portion 210 by a depth d. In this way, the thickness of second lens portion 220 at any distance from the center of lens 200 is less than the thickness of first lens portion 210 at that distance. This difference in thicknesses of first lens portion 210 and second lens portion 220 can result in the incident planar acoustic waves to be transmitted differently through each portion.

Of course, regardless of the specific configuration, modifying lens 200 in this way by truncating an outer rim portion of lens 200 can broaden the focal width of the acoustic field of the shock wave at focus F. In particular, because the size of first portion 210 can be comparatively smaller than the total size of previous lenses, this relative reduction in the numerical aperture for a given focal length can result in a broader focal width W given by the following relationship:

$$W = k\frac{f}{d}\lambda$$

where d is the aperture dimension, f is the focal length, λ is the wavelength of the acoustic shock wave, and k is a constant. This broadened focal width can better account for the effect of dispersion of stone fragments as repeated shock waves break up the target object. Further, a broad focal width can be desirable where target T can move away from beam focus F, such as when initial shock waves cause the target object to move from its original location or when a lithotripsy patient breathes.

In addition, those having skill in the art will recognize that other methods for delaying the propagation of a portion of the shock wave can be used to achieve the advantages discussed herein, including the use of multiple lenses, lenses composed of multiple materials, or acoustic barrier materials that can block portion of the original lens surface while enhancing the generation of diffractive waves at the edges of the barriers.

Figure 4A:
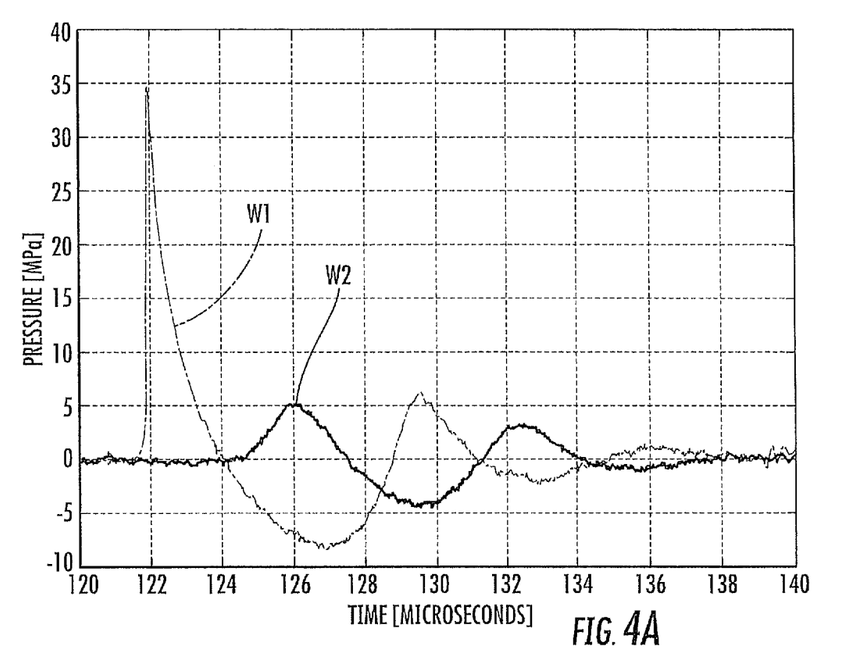
FIG. 4A is a pressure versus time graph of two acoustic pressure waveforms generated by an acoustic lens according to an embodiment of the presently disclosed subject matter.
Figure 4B:
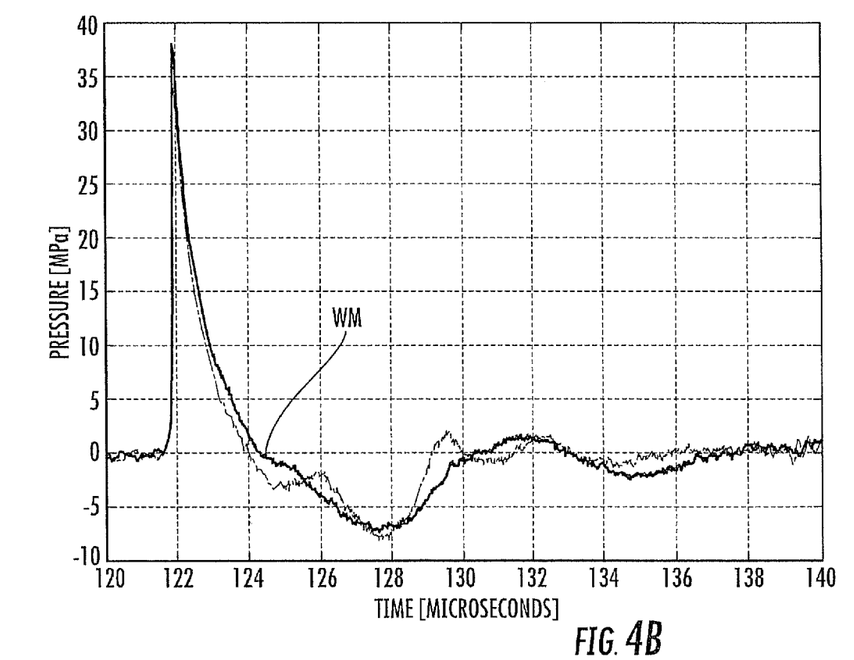
FIG. 4B is a pressure versus time graph of two samples of a combined pressure waveform generated by an acoustic lens according to an embodiment of the presently disclosed subject matter.

Regardless of the specific form of acoustic lens 200, with lens 200 being modified as discussed above, the original acoustic pulse generated by shock wave source 300 can be partitioned into multiple pulses. Referring to FIG. 4A, a first shock wave W1 can be produced by first lens portion 210 (e.g., the central portion) of acoustic lens 200, first shock wave W1 including a first leading compressive component, a tensile component, and a second trailing compressive component. An ensuing second shock wave W2 can be produced by second lens portion 220 of acoustic lens 200, second shock wave W2 having a similar wave profile to first shock wave W1. Specifically, for example, second shock wave W2 shown in FIG. 4A can be produced with second lens portion 220 being an outer rim of acoustic lens 200 (e.g., comprising about 35% of the original area), the outer rim being truncated (e.g., to a groove depth d of about 13.5 mm). Both first shock wave W1 and second shock wave W2 can be directed generally towards beam focus F where target T can be positioned (e.g., a concretion within a living body).

The geometric differences between first lens portion 210 and second lens portion 220 can cause first shock wave W1 to propagate through first lens portion 210 faster than second shock wave W2 can propagate through second lens portion 220. Because the sound speed in the acoustic lens is higher than that in the coupling fluid (e.g., water, oil, silicone), this difference can result in a very short delay in the propagation of second shock wave W2 from lens 200 relative to first shock wave W1, which can range between about 0.1 to about 10 microseconds, and particularly between about 1.5 and 6 microseconds.

As noted above, previous modifications to shock-wave lithotripsy systems have involved the use of multiple shock-wave pulses that are separated by a time delay. The multiple pulses of these methods, however, are created by modifications to the shock-wave source or by the use of additional acoustic lenses to create multiple, separate shock wave pulses. As a result, the creation of these multiple shock-wave pulses requires modification to the shock-wave source and/or the inclusion of additional components, both of which can require time and energy in the adjustment and modification of the system beyond the mere substitution of a single acoustic lens. In addition, the previous modifications were not aimed to change the profile of the pressure waveform while simultaneously broadening the focal width of the lithotripter field.

In contrast, using the presently-disclosed systems and methods, multiple shock-wave pulses are created by modifying the geometry of lens 200. The length of the delay in the propagation of second shock wave W2 relative to first shock wave W1 can be varied depending on a number of factors, including the geometry of lens 200 and the properties of the coupling fluid in which the shock waves produced by the lithotripsy system propagate. For instance, in embodiments where second lens portion 220 is modified by including groove 222, the length of the delay can be correlated to depth d of groove 222. The tandem pulse of these two waves can then be superimposed to produce a modified waveform WM at target T with a much reduced second compressive wave component and a significantly increased lithotripter focal width. Specifically, the second compressive portion of first shock wave W1 can be reduced by the in situ superposition with the tensile component of the trailing second shock wave W2. In this way, the acoustic field, cavitation activity, and stone comminution produced by the modified lens design can result in significant improvement in stone comminution as compared to typical lens designs under comparable total acoustic pulse energy.

Figure 5A:
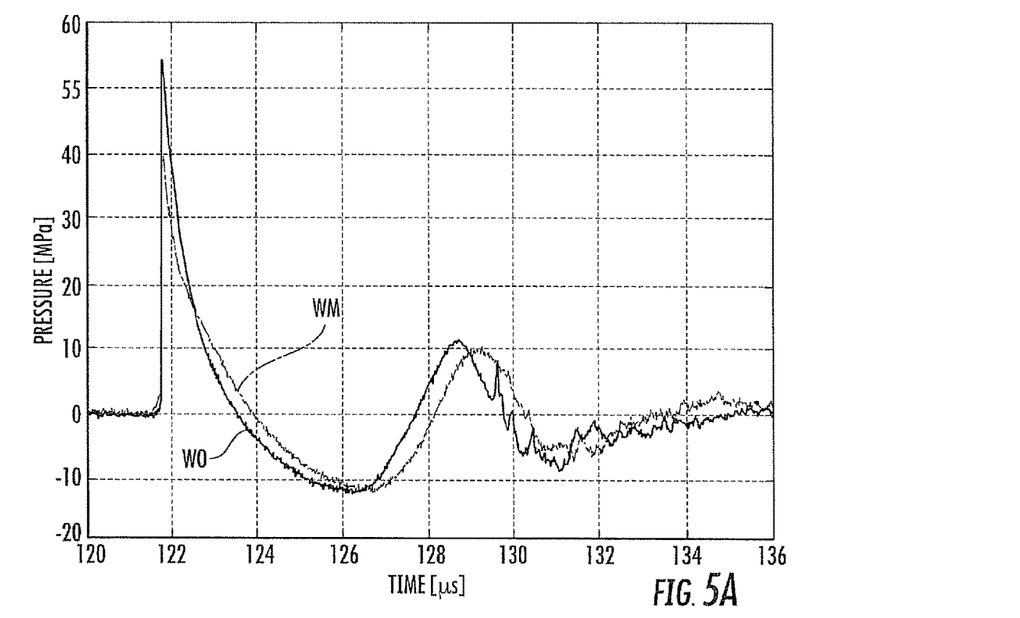
FIGS. 5A and 5B are pressure versus time graphs of different samples of a pressure waveform generated by a typical acoustic lens compared to a modified pressure waveform generated by an acoustic lens according to an embodiment of the presently disclosed subject matter.

FIG. 5A shows a comparison of a waveform produced by a previous design for an acoustic lens, generally designated WP, and a modified waveform WM at 15.8 kV using a modified lens with 65% area ratio and a groove depth d of about 6 mm. Using these parameters, although the waveform profile does not change appreciably, a reduction in the peak positive pressure (p+) is achieved, which in turn can result in an increase in focal width with a concomitant reduction of the effective acoustic pulse energy. Of course, it should be understood that higher levels of p+ can be achieved by increasing the initial output voltage from shock wave source 300 to compensate for the reduction in p+ that results from the partitioning of the shock wave pulse.

Figure 5B:
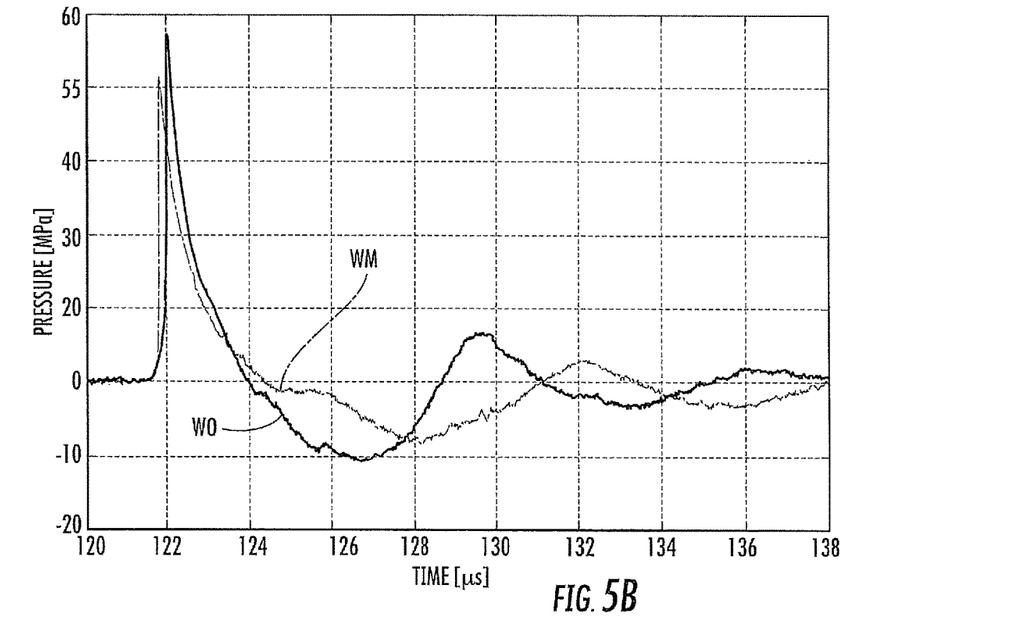

To achieve a better suppression of the second compressive peak, the delay can be prolonged between the waves W1 and W2 produced by lens 200. For example, referring to FIG. 5B, the comparison of previous waveform WP to modified waveform WM shows a significant decrease in the size of the second compressive peak in modified waveform WM at the beam focus F. In this instance, the delay between first shock wave W1 and second shock wave W2, which contributes to the suppression of the second compressive peak, is extended by an increase in the groove depth d (e.g., to about 14.5 mm).

Table 1 summarizes the measurement results and derived parameters for the original and modified lenses in the range of 13.8 to 16.8 kV. The modified lens can be further trimmed, for example to about a 60% area ratio with a groove depth d of about 14.5 mm. The effective acoustic pulse energy measured by E(12 mm) are comparable between the original lens at 13.8 kV with an energy level of 54.2 mJ and the modified lens at 16.8 kV with an energy level of 52.1 mJ. A significant truncation of the second compressive peak is achieved with a concomitant reduction in p+ at the beam focus, which leads to a broader focal width (e.g., increasing from about 7.3 mm for the original lens to about 10.7 mm for the modified lens). In particular, at a small radial distance from focus F (e.g., about 6 to 10 mm), the second compressive wave can be completely eliminated from acoustic signals transmitted through lens 200. Furthermore, p+ for lens 200 at a small radial distance form focus F (e.g., greater than about 6 mm) can be higher than for previous acoustic lens 100, which can be a result of a stronger shock wave-bubble interaction and thus a better synergy between stress waves and cavitation in stone comminution at these locations.

TABLE 1

Acoustic field parameters of the original and modified lenses

| Lens | Output (kV) | P+ (MPa) | \|P−\| (MPa) | −6 dB focal width (mm) | Energy [12 mm] (mJ) |
|---|---|---|---|---|---|
| Original | 13.8 | 46.3 ± 0.6 | 10.9 ± 0.8 | 7.3 ± 0.2 | 54.2 |
| Modified | 16.8 | 41.4 ± 1.1 | 8.9 ± 0.4 | 10.7 ± 0.2 | 52.1 |

The modified lens can exhibit a lower energy density at the central axis (e.g., about 0.57 mJ/mm$^2$) compared to the energy density produced using the original lens (e.g., about 0.72 mJ/mm$^2$), but its decay can also be much slower along the radial direction. It has been discovered that at a small radial distance from focus F (e.g., about 6 mm), the energy densities produced by the two lens systems can be substantially equivalent, and beyond that small distance lens 200 can have a higher energy density than previous acoustic lens 100. Such changes in energy density distribution of the modified lens can reduce the risk of tissue injury while potentially increasing comminution efficiency of dispersed fragments (off-axis) during SWL.

We have now found that the design of lens 200 can optimize the pressure waveform profile of the lithotripter pulse generated by an electromagnetic shock wave source 300 and can further simultaneously enlarge the focal width of the focused shock wave WM that it generates, which can lead to improved stone comminution with reduced tissue injury. Further, these advantages can be realized by implementing the minimal design changes disclosed herein (i.e., by modification of acoustic lens geometry), thereby achieving two important goals in lithotripter shock source design, namely pulse profile optimization and focal width enlargement, through a single modification.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter. For instance, the principles of modifying the shock waves generated by an electromagnetic source can be applied to different source configurations known in the art, including, for example, the cylindrical coil source described in U.S. Pat. No. 5,058,569 to Hassler et al. or the spherically-calotte shaped source described in U.S. Pat. No. 4,669,472 to Eisenmenger.

What is claimed is:

1. An acoustic lens for a shock wave lithotripter having a maximum pressure, said acoustic lens comprising:
a first lens portion comprising a center portion of said acoustic lens, said first lens portion having a first concave geometry configured to produce a first shock wave from an acoustic shock wave pulse generated by an electromagnetic shock wave pulse generator and directing said first shock wave toward a target, said first shock wave comprising a first leading compressive component, a tensile component, and a second trailing compressive component; and
a second lens portion comprising an outer rim portion of said acoustic lens, said second lens portion having a second concave geometry configured to produce a second shock wave from said acoustic shock wave pulse and directing said second shock wave toward said target, said second shock wave comprising a first leading compressive component, a tensile component, and a second trailing compressive component, said second lens portion comprising a groove formed in a surface of said outer rim portion that is offset relative to a surface of said first lens portion by a depth d such that transmission of said second shock wave through said second lens portion is delayed by a predetermined amount Δt relative to transmission of said first shock wave through said first lens portion;
wherein said offset is selected based on a relationship between the predetermined amount Δt and the depth d, a speed of sound $c_0$ in a coupling fluid with which the acoustic lens is to be used, and a speed of sound $c_{lens}$ in a material from which the acoustic lens is composed:

$$\Delta t = d\left(\frac{1}{c_0} - \frac{1}{c_{lens}}\right)$$

wherein said tensile component of said second shock wave is superimposed with said second trailing compressive component of said first shock wave to produce a modified waveform comprising a second trailing compressive component having a reduced magnitude relative to a second trailing compressive component of said acoustic shock wave pulse;
wherein said predetermined amount Δt is between 0.1 and less than 10 microseconds;
wherein the depth d is between 5 mm and 25 mm;
wherein said first lens portion comprises between 50% and 75% of a total transmissive or reflective area of said acoustic lens; and
wherein said maximum pressure is in the range from 5 to 200 MPa.

2. A system for shock wave lithotripsy comprising:
an electromagnetic shock wave pulse generator for generating an acoustic shock wave pulse;
an acoustic lens positioned between said shock wave pulse generator and a target, said acoustic lens comprising:
a first lens portion comprising a center portion of said acoustic lens, said first lens portion being configured for producing a first shock wave from said acoustic shock wave pulse and directing said first shock wave toward said target, said first shock wave comprising a first leading compressive component, a tensile component, and a second trailing compressive component; and
a second lens portion comprising an outer rim portion of said acoustic lens, said second lens portion being configured for producing a second shock wave from said acoustic shock wave pulse and directing said second shock wave toward said target, said second shock wave comprising a first leading compressive component, a tensile component, and a second trailing compressive component, said second lens portion comprising a groove formed in a surface of said outer rim portion that is offset relative to a surface of said first lens portion by a depth d such that transmission or reflection of said second shock wave through or by said second lens portion is delayed by a predetermined amount Δt relative to transmission or reflection of said first shock wave through or by said first lens portion based on a relationship between the predetermined amount Δt and the depth d, a speed of sound $c_0$ in a coupling fluid with which the acoustic lens is to be used, and a speed of sound $c_{lens}$ in a material from which the acoustic lens is composed:

$$\Delta t = d\left(\frac{1}{c_0} - \frac{1}{c_{lens}}\right)$$

wherein said tensile component of said second shock wave is superimposed with said second trailing compressive component of said first shock wave to produce a modified waveform comprising a second trailing compressive component having a reduced magnitude relative to a second trailing compressive component of said acoustic shock wave pulse, wherein said predetermined amount $\Delta t$ is between 0.1 and less than 10 microseconds, and wherein the depth d is between 5 mm and 25 mm.

3. The system of claim 2, wherein said shock wave pulse generator comprises an electromagnetic coil.

4. The system of claim 2, wherein said groove is formed in a surface of said second lens portion facing said shock wave pulse generator.

5. The system of claim 2, wherein said groove is formed in a surface of said second lens portion facing said target.

6. The acoustic lens of claim 1, wherein the acoustic lens is configured to produce a maximum energy density that is greater than 0 and less than 0.72 mJ/mm$^2$.

7. The acoustic lens of claim 1, wherein the acoustic lens is configured to produce a minimum beam width in a range of greater than 7.3 mm to less than or equal to 10.7 mm.

8. The acoustic lens of claim 1, wherein the predetermined amount is between 1.5 and 6 microseconds.

9. The system of claim 2, wherein the predetermined amount is between 1.5 and 6 microseconds.

* * * * *